United States Patent [19]

Wong et al.

[11] 4,127,127

[45] Nov. 28, 1978

[54] THERAPEUTIC SYSTEMS MADE FROM CERTAIN SEGMENTED COPOLYESTERS

[75] Inventors: Patrick S. L. Wong; Kelly L. Smith, both of Palo Alto; Alan S. Michaels, Atherton, all of Calif.

[73] Assignee: Alza Corporation, Palo Alto, Calif.

[21] Appl. No.: 799,854

[22] Filed: May 23, 1977

[51] Int. Cl.² .............................................. A61M 31/00
[52] U.S. Cl. .................................... 128/260; 128/130; 128/213; 128/272; 424/19
[58] Field of Search ............... 128/130, 260, 213, 272; 424/19

[56] References Cited

U.S. PATENT DOCUMENTS

| 3,651,014 | 3/1972 | Witsiepe | 260/75 R |
| 3,763,109 | 10/1973 | Witsiepe | 260/33.8 R |
| 3,766,146 | 10/1973 | Witsiepe | 260/40 R |
| 3,832,458 | 8/1974 | Merrill | 128/260 |
| 3,895,103 | 7/1975 | Zaffaroni | 128/130 |
| 3,948,262 | 4/1976 | Zaffaroni | 128/130 |
| 3,993,072 | 11/1976 | Zaffaroni | 128/130 |
| 3,993,073 | 11/1976 | Zaffaroni | 128/130 |

Primary Examiner—Benjamin R. Padgett
Assistant Examiner—Christine M. Nucker
Attorney, Agent, or Firm—Thomas E. Ciotti; Paul L. Sabatine; Edward L. Mandell

[57] ABSTRACT

Therapeutic systems in the form of drug-containing bags or packets made from films of segmented copolyesters of butylene terephthalate and polyalkylene ether terephthalate are disclosed.

13 Claims, 4 Drawing Figures

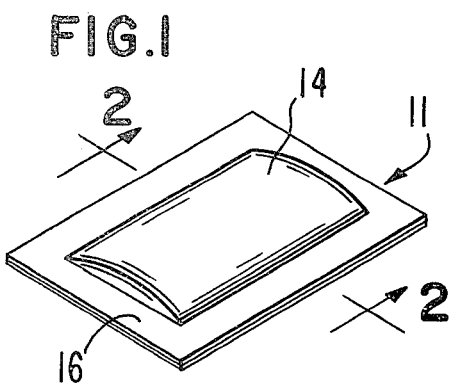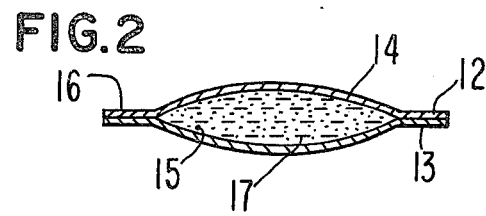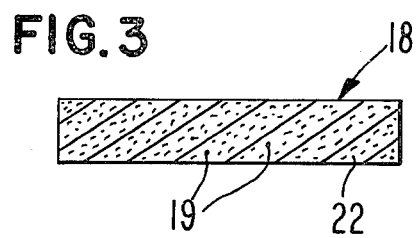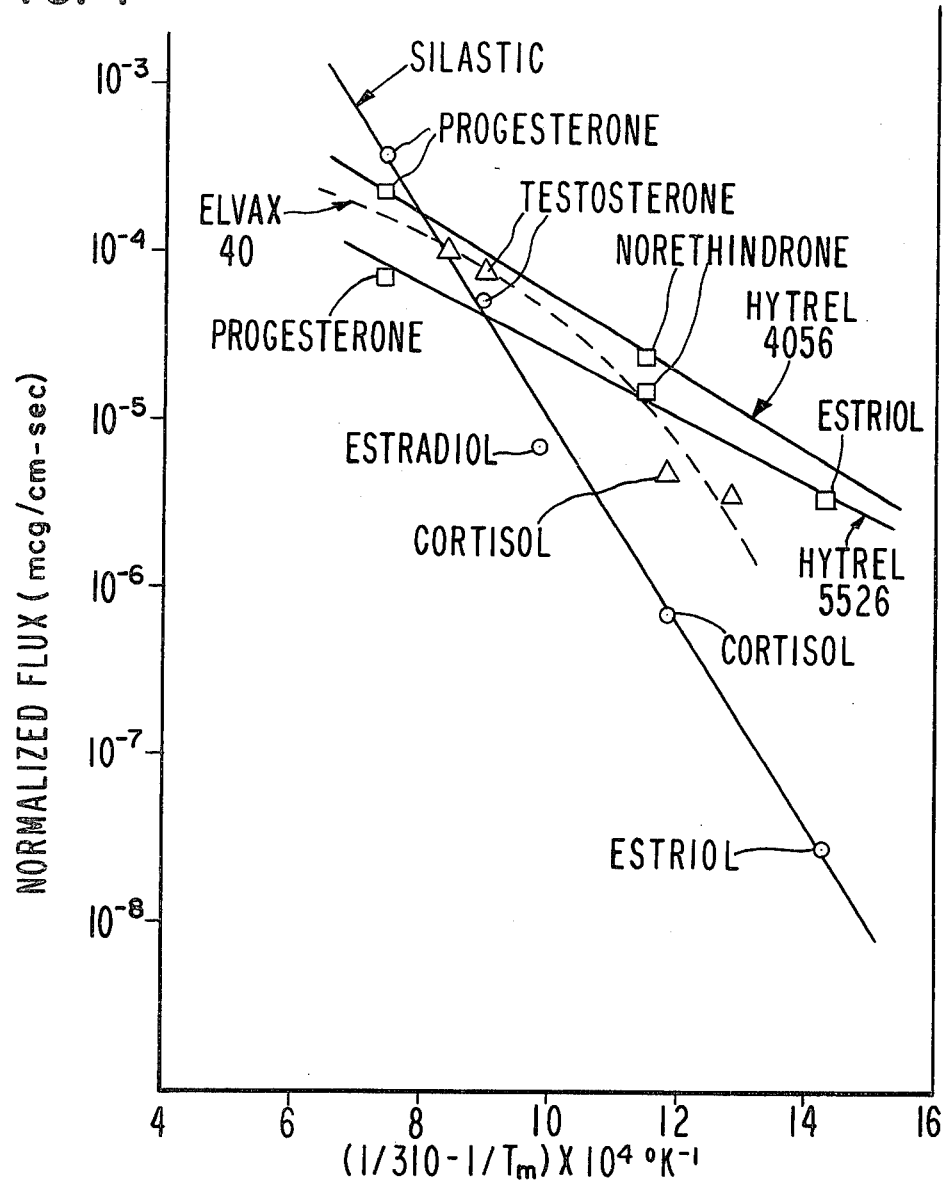

THERAPEUTIC SYSTEMS MADE FROM CERTAIN SEGMENTED COPOLYESTERS

BACKGROUND OF THE INVENTION

1. Field of the Invention

The invention concerns diffusional active agent delivery systems in which the polymer through which the drug diffuses is a segmented copolyester.

2. Description of the Prior Art

Diffusional therapeutic systems (drug delivery devices) comprising a drug confined in a polymer that is permeable to the drug are well known. Drug is released from such systems by diffusing through the polymer at a controlled rate in accordance with Fick's law. Structurally these systems may be of the monolithic type or the reservoir type. In monolithic systems the drug is dispersed throughout a matrix of the polymer. In reservoir systems the polymer is in the form of a wall that defines a capsule in which the drug, either neat or mixed with a solid or liquid carrier, is held.

Of the many polymers suggested for use in diffusional therapeutic systems, silicone rubbers such as polydimethylsiloxanes, and ethylene-vinyl acetate copolymers have probably been the most popular. However, even such rubbers and copolymers have disadvantages. One such disadvantage is that high, controlled release rates of drug (by diffusion) may not be achieved using such materials. This is due primarily to the fact that it is not possible to form very thin-walled capsules from these materials that have sufficient wall strength to be useful in vivo as a drug dispenser. Another disadvantage is that these materials are substantially impermeable to drugs that have significant hydrogen binding or induced dipole forces. Thus, it is not practicable to release such drugs by diffusion from these materials.

SUMMARY OF THE INVENTION

One aspect of the invention is an improvement in active agent delivery systems comprising an active agent confined within a polymer that is substantially permeable to the active agent. The improvement is the use as the polymer component of the system of a segmented thermoplastic copolyester elastomer consisting essentially of a multiplicity of recurring long chain ester units and short chain ester units joined head-to-tail through ester linkages, the long chain ester units being of the formula:

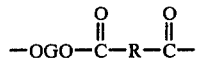

(1)

and the short chain ester units being of the formula:

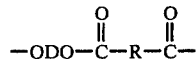

(2)

where G is a divalent radical remaining after the removal of terminal hydroxyl groups from a poly(alkylene oxide) glycol having a molecular weight of about 400 to 4000 and a carbon-to-oxygen ratio of about 2.0 to 4.3, R is a divalent radical remaining after removal of carboxyl groups from a dicarboxylic acid having a molecular weight less than about 300, and D is a divalent radical remaining after removal of hydroxyl groups from a diol having a molecular weight less than about 250, provided the short chain ester units constitute about 30% to about 90% by weight of the copolyester, at least about 70% of the radicals represented by D are 1,4-butylene radicals and at least about 70% of the radicals represented by R are 1,4-phenylene radicals, with the sum of the percentages of R radicals which are not 1,4-phenylene radicals and of the D radicals which are not 1,4-butylene radicals not exceeding about 30.

Another aspect of the invention is a therapeutic system for administering drug to a body site comprising a packet that is sized and shaped for placement at said site and is formed from two films, at least one of which is made of the above described copolyester, the two films being spaced from each other at a central portion so as to form a cavity and being sealed together at their edges to sealingly close the cavity, and drug contained within the cavity to which the film that is made of the copolyester is substantially permeable.

BRIEF DESCRIPTION OF THE DRAWINGS

In the drawings:

FIG. 1 is an enlarged dimetric view of an embodiment of the improved system of the invention that may be used to administer drugs gastrointestinally;

FIG. 2 is an enlarged sectional view taken along line 2—2 of FIG. 1;

FIG. 3 is an enlarged sectional view of another embodiment of the improved systems of this invention; and FIG. 4 is a graph showing the fluxes of various drugs through the segmented copolymer of the systems of this invention as compared to the fluxes of various drugs through an ethylene-vinyl acetate copolymer and silicone rubber.

DETAILED DESCRIPTION OF THE INVENTION

The above described copolyesters of the improved systems of the invention are known and are available commercially under the trademark HYTREL. These polymers and methods for preparing them are described in U.S. Pat. Nos. 3,651,014; 3,763,109, and 3,766,146. The disclosure of these patents with respect to the manufacture, composition, and properties of the polymers is incorporated herein by reference.

Preferred copolyesters for use in the invention systems are those wherein the short chain ester units constitute about 30% to about 60% by weight of the copolyester, G in formula (1) is a poly(alkyleneoxy) radical wherein the alkylene group is of 2 to 4 carbon atoms, all of the D radicals of formula (2) are 1,4-butylene, and all of the R radicals of both formulas are 1,4-phenylene. Of these preferred copolyesters those wherein G in formula (1) is a poly(tetramethyleneoxy) radical having a molecular weight of 800 to 1200 are particularly preferred.

The above described copolyester may be used to make therapeutic systems such as those shown in FIGS. 1-3. The system of FIGS. 1 and 2, generally designated 11, consists of two rectangular thin sheets or films 12, 13, at least one of which is made of the above described copolyester, placed face-to-face. Films 12, 13 are spaced from each other at a central portion 14 so as to form a pocket or cavity 15. They are heat-sealed together at their peripheries 16 to close pocket 15. Pocket 15 contains a drug composition 17 that may consist of neat drug or, preferably, drug admixed with a solid, semi-solid (e.g. gel) or liquid carrier. When composition 17 consists of a drug-carrier mixture it is preferable that the carrier be substantially more permeable (i.e. at least 10 times as permeable) to the drug than are films 12, 13 and that the drug be present in a sufficient amount to keep the carrier saturated with drug over the drug-dispensing lifetime of system 11.

Films 12, 13 may be made of the same copolyester or of two different copolyesters. Alternatively one of films 12, 13 may be made from a different material (e.g. a polymer other than one of the above described copolyesters) that is either permeable or impermeable to the drug. Preferably, both are made of the same copolyester. While system 11 is shaped as a parallelipiped and is sized to be taken orally, it may be shaped and sized otherwise, with the particular size and shape being dictated by the body site at which it is to be placed. Systems such as system 11 may also be made by forming the copolyester into thin walled tubing, such as by extrusion, filling the tubing with drug, and sealing the ends of the tubing.

FIG. 3 depicts a monolithic-type therapeutic system, generally designated 18. System 18 consists of a dispersion of drug particles 19 in a matrix 22 of said copolyester. System 18 is in the form of a solid body that is sized and shaped for placement at the body site at which the drug is to be dispensed.

Systems 11 and 18 release drug by diffusion. In the case of device 11, drug contained in pocket 15 dissolves in the copolyester forming film 12 and/or film 13 and diffuses outwardly through film 12 and/or film 13, as the case may be. Assuming the concentration of drug at the inner surfaces of films 12 and/or 13 is constant and, if the drug is mixed with a carrier that the carrier is more permeable to drug than are films 12 and/or 13, the rate at which the drug diffuses through films 12 and/or 13 will depend upon the solubility of the drug in the copolyester forming the film, the diffusion coefficient of the drug in the copolyester, and the thickness of the film. The thickness of the copolyester film will usually be in the range of about 0.01 to 0.5 mm. The rate of drug release from such a system will be substantially constant.

In system 18 drug 19 simply dissolves in and permeates outwardly through surrounding matrix 22. The rate of drug release from such a system is proportional to time $^{-\frac{1}{2}}$.

The improved systems of the invention may be used to dispense by diffusion most nonionic forms of drugs having a molecular weight less than about 1000. Included within the drugs that may be dispensed from the invention systems are those having significant hydrogen bonding or induced dipole forces. These drugs are sometimes categorized as being "polar" and are normally characterized by having a melting point greater than about 170° C. and a hydrogen bonding component, $\delta_H$, of a multicomponent solubility parameter greater than about 5 cal$^{\frac{1}{2}}$ cm$^{-3/2}$. If desired the copolyester may be made more permeable to nonionic drugs by incorporating water insoluble liquid plasticizers into the copolyester. These additives "soften" the copolyester (causing its diffusion coefficient to increase) but do not leach out of the copolyester. These plasticizers may be used in amounts ranging from 2% to 60% by weight based on the copolyester. Preferred water insoluble liquid plasticizers are butylene glycol-adipic acid copolymers (sold under the designation SANTICIZER) and poly (propylene glycol).

The copolyester also may be made water-permeable and microporous in situ and thus capable of dispensing ionic forms of drugs or high molecular weight drugs (MW above about 1000) by incorporating water-leachable plasticizers into the copolyester. (The copolyester itself is substantially impermeable to such drugs). Such additives leach slowly from the copolyester to create a water-swollen microporous structure. These water leachable plasticizers may be incorporated in amounts from 2% up to 60% by weight based on the copolyester without impairing the mechanical (tensile) properties of the copolyester significantly. Preferred water leachable plasticizers are ethylene oxide-propylene oxide block copolymers (sold under the designation PLURONIC).

EXAMPLES

The following examples illustrate the invention. They are not intended to limit the invention in any manner. Unless indicated otherwise, proportions are by weight.

EXAMPLE 1

The permeability of a segmented copolymer of butylene terephthalate, 33%, and polytetramethylene ether terephthalate (MW 1132), 67%, (sold under the brand name HYTREL 4056) and a segmented copolymer of butylene terephthalate, 58%, and polytetramethylene ether terephthalate (MW 1132), 42%, (sold under the brand name HYTREL 5526) as compared to silicone rubber (sold under the brand name SILASTIC) and to an ethylene-vinyl acetate copolymer 40%, vinyl acetate, (sold under the brand name ELVAX 40) was determined by making 0.2 mm thick membranes of each polymer, placing the membranes into diffusion cells maintained at 37° C. containing various drugs, and measuring the drug flux through the membrane spectrophotometricaly. FIG. 4 is a logarithmic plot of the results of these tests, with normalized flux (defined as saturated drug solution upstream separated by a membrane with infinite dilution downstream) plotted against a temperature function of the melting point, Tm, of the drug. As shown, the segmented copolymer has a much greater permeability to high melting drugs than either of the two comparison polymers.

EXAMPLES 2–9

Therapeutic systems of the type shown in FIGS. 1 and 2 were made as follows: Films of the segmented copolymer of Example 1, 0.05 mm thick, were melt-pressed. Square pieces (30 × 30 mm) were cut from the film. Pairs of these pieces were placed face-to-face and their edges (about 2–3 mm border) on three sides were heat-sealed together to form small pockets or bags. The bags were filled with the drug compositions listed in Table 1 and the fourth sides of the bags were sealed. The drug release from the bags was measured by placing the bags in saline at 37° C. with agitation for a given time period and measuring the drug concentration in the saline by UV spectrophotometry. The results of these measurements are indicated in Table 1.

TABLE 1

| Ex. # | Drug | Carrier, Amount | Drug Release (mg/cm$^2$ hr) |
|---|---|---|---|
| 2 | Progesterone | Pluronic L64*, 30% | 0.10 |
| 3 | Estradiol | Pluronic L64*, 30% | 0.021 |
| 4 | Aspirin | PPG** MW 2000, 30% | 0.66 |
| 5 | Hydrocortisone Alcohol | Water Slurry | 0.01 |
| 6 | Chloramphenicol | Water Slurry | 0.14 |
| 7 | Pilocarpine-base | Pure Liquid Drug | 0.17 |
| 8 | Diazepam (Valium) | PPG** MW 2000, 33% | 0.19 |
| 9 | Indomethacin | PPG** MW 2000, 30% | 0.11 |

TABLE 1-continued

| Ex. # | Drug | Carrier, Amount | Drug Release (mg/cm² hr) |
|---|---|---|---|
| | (Indocin) | | |

*ethylene oxide-propylene oxide copolymer
**poly(propylene glycol)

EXAMPLE 10

To illustrate the increase in drug permeation that may be achieved by adding water insoluble plasticizers to the segmented copolymer, Example 2 was repeated with 20% and 50% of a linear polyester, MW 2000, plasticizer (sold under the trade designation SANTICIZER 334 F) added to the copolymer. The drug release from the 20% SANTICIZER 334 F bag was 0.20 mg/cm² hr. and from the 50% SANTICIZER 334 F bag 0.23 mg/cm² hr.

EXAMPLE 11

Example 9 was repeated with 50% ethylene oxide-propylene oxide copolymer (sold under the trade designation Pluronic F103) as the carrier and with 20% poly(propylene glycol) (MW 2000) added to the segmented copolymer. The drug release was 0.32 mg/cm² hr.

EXAMPLES 12-17

Modification of the copolyesters with water-leachable plasticizers was carried out as follows. Bags (approximately 75 microns thick instead of 50 microns) were made as in Examples 2-11 with the addition of ethylene oxide-propylene oxide copolymer plasticizer (sold under the trade designation Pluronic F127) to the segmented copolymer in the amounts shown in Table 2. The bags were filled with the drugs shown in Table 2 in pure, micronized form and the fourth sides of the bags were heat-sealed. Drug release from the bags was measured as in Examples 2-11. These measurements are listed in Table 2.

Table 2

| Example # | Drug | % Pluronic Plasticizer | Drug Release (mg/cm² hr) |
|---|---|---|---|
| 12 | Pilocarpine-Nitrate | 5 | 0.005 |
| 13 | | 15 | 0.082 |
| 14 | | 25 | 0.93 |
| 15 | Propoxyphene HCl (Darvon) | 40 | 2.70 |
| 16 | Tetracycline HCl | 25 | 0.33 |
| 17 | Tetracycline HCl | 40 | 1.40 |

EXAMPLE 18

A bag was made as in Examples 15 and 17. Methyldopa mixed with polyacrylic acid carrier (40%) was placed in the bag and the fourth side of the bag was sealed. The membrane consisted of 40% Pluronic plasticizer added to the segmented copolymer. Drug release was measured as in the previous examples and was found to be 0.77 mg/cm² hr.

EXAMPLE 19

Example 18 was repeated with 30% Pluronic plasticizer added to the segmented copolymer (instead of 40%) and with the ethylester HCl form of methyldopa. Drug release was 4.8 mg/cm² hr.

Although the invention has been descibed in detail only with respect to embodiments that release drugs, it is apparent that embodiments that disseminate other active agents, i.e. compositions that have a beneficial effect on their site of administration, such as pesticides, herbicides, algicides, nutrients, catalysts, and the like are feasible. Such embodiments as well as modifications of the invention that are obvious to those of skill in the medical, pharmaceutical, polymer, and related arts are intended to be within the scope of the following claims.

We claim:

1. A therapeutic system for administering drug to a body site comprising a packet that is sized and shaped for placement at said site and is formed from:

(a) two films, at least one of which is made of a segmented thermoplastic copolyester elastomer consisting essentially of a multiplicity of recurring long chain ester units and short chain ester units joined head-to-tail through ester linkages, the long chain ester units being of the formula:

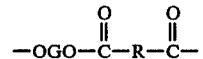

and the short chain ester units being of the formula:

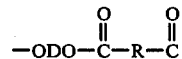

where G is a divalent radical remaining after the removal of terminal hydroxyl groups from a poly(alkylene oxide) glycol having a molecular weight of about 400 to 4000 and a carbon-to-oxygen ratio of about 2.0 to 4.3, R is a divalent radical remaining after removal of carboxyl groups from a dicarboxylic acid having a molecular weight less than about 300, and D is a divalent radical remaining after removal of hydroxyl groups from a diol having a molecular weight less than about 250, provided the short chain ester units constitute about 30% to about 90% by weight of the copolyester, at least about 70% of the radicals represented by D are 1,4-butylene radicals and at least about 70% of the radicals represented by R are 1,4-phenylene radicals, with the sum of the percentages of R radicals which are not 1,4-phenylene radicals and of the D radicals which are not 1,4-butylene radicals not exceeding about 30%, the two films being spaced from each other at a central portion so as to form a cavity and being sealed together at their edges to sealingly close the cavity; and (b) drug contained within said cavity to which said one of said films is substantially permeable.

2. The therapeutic system of claim 1 wherein both films are made of said copolyester.

3. The therapeutic system of claim 1 wherein the short chain ester units constitute about 30% to about 60% by weight of the copolyester, G is a poly(alkyleneoxy) radical wherein the alkylene group is of 2 to 4 carbon atoms, all of the D radicals are 1,4-butylene, and all of the R radicals are 1,4-phenylene.

4. The therapeutic system of claim 3 wherein G is a poly(tetramethyleneoxy) radical having a molecular weight of 800 to 1200.

5. In an active agent delivery system comprising an active agent confined within a polymer that is substantially permeable to the active agent, the improvement wherein said polymer is a segmented thermoplastic copolyester elastomer consisting essentially of a multiplicity of recurring long chain ester units and short chain ester units joined head-to-tail through ester linkages, the long chain ester units being of the formula:

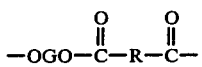

and the short chain ester units being of the formula:

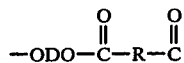

where G is a divalent radical remaining after the removal of terminal hydroxyl groups from a poly(alkylene oxide) glycol having a molecular weight of about 400 to 4000 and a carbon-to-oxygen ratio of about 2.0 to 4.3, R is a divalent radical remaining after removal of carboxyl groups from a dicarboxylic acid having a molecular weight less than about 300, and D is a divalent radical remaining after removal of hydroxyl groups from a diol having a molecular weight less than about 250, provided the short chain ester units constitute about 30% to about 90% by weight of the copolyester, at least about 70% of the radicals represented by D are 1,4-butylene radicals and at least about 70% of the radicals represented by R are 1,4-phenylene radicals, with the sum of the percentages of R radicals which are not 1,4-phenylene radicals and of the D radicals which are not 1,4-butylene radicals not exceeding about 30%.

6. The improvement of claim 5 wherein the short chain ester units constitute about 30% to about 60% by weight of the copolyester, G is a poly(alkyleneoxy) radical wherein the alkylene group is of 2 to 4 carbon atoms, all of the D radicals are 1,4-butylene, and all of the R radicals are 1,4-phenylene.

7. The improvement of claim 6 wherein G is a poly(tetramethyleneoxy) radical having a molecular weight of 800 to 1200.

8. The improvement of claim 6 wherein the active agent is a nonionic drug having a molecular weight less than about 2000.

9. The improvement of claim 8 wherein the drug has a melting point greater than about 170° C. and a hydrogen bonding component of a multicomponent solubility parameter greater than about 5 cal$^{\frac{1}{2}}$ cm$^{-3/2}$.

10. The improvement of claim 8 wherein the copolyester is plasticized with about 2% to about 60% of a water insoluble liquid plasticizer.

11. The improvement of claim 10 wherein the plasticizer is a butylene glycol-adipic acid copolymer.

12. In an active agent delivery system comprising an active agent confined within a polymer, the improvement wherein the polymer is a segmented thermoplastic copolyester elastomer consisting essentially of a multiplicity of recurring long chain ester units and short chain ester units joined head-to-tail through ester linkages, the long chain ester units being of the formula:

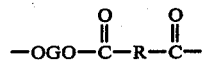

and the short chain ester units being of the formula:

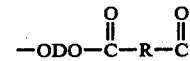

where G is a divalent radical remaining after the removal of terminal hydroxyl groups from a poly(alkylene oxide) glycol having a molecular weight of about 400 to 4000 and a carbon-to-oxygen ratio of about 2.0 to 4.3, R is a divalent radical remaining after removal of carboxyl groups from a dicarboxylic acid having a molecular weight less than about 300, and D is a divalent radical remaining after removal of hydroxyl groups from a diol having a molecular weight less than about 250, provided the short chain ester units constitute about 30% to about 90% by weight of the copolyester, at least about 70% of the radicals represented by D are 1,4-butylene radicals and at least about 70% of the radicals represented by R are 1,4-phenylene radicals, with the sum of the percentages of R radicals which are not 1,4-phenylene radicals and of the D radicals which are not 1,4-butylene radicals not exceeding about 30%, and the copolyester is plasticized with about 2% to about 60% of a water leachable plasticizer.

13. The improvement of claim 12 wherein the plasticizer is an ethylene oxide-propylene oxide block copolymer.

* * * * *